United States Patent
Zhu et al.

(10) Patent No.: US 9,421,522 B2
(45) Date of Patent: Aug. 23, 2016

(54) IRIDIUM CATALYSTS FOR CARBONYLATION

(71) Applicant: Eastman Chemical Company, Kingsport, TN (US)

(72) Inventors: Zhidong George Zhu, Kingsport, TN (US); Gerald Charles Tustin, Kingsport, TN (US); Joseph Robert Zoeller, Kingsport, TN (US); Mary Kathleen Moore, Jonesborough, TN (US); David Alan Jenkins, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 507 days.

(21) Appl. No.: 13/716,336

(22) Filed: Dec. 17, 2012

(65) Prior Publication Data

US 2013/0172601 A1 Jul. 4, 2013

Related U.S. Application Data

(60) Provisional application No. 61/580,818, filed on Dec. 28, 2011.

(51) Int. Cl.

| | | |
|---|---|---|
| *C07C 67/36* | (2006.01) |
| *C07C 51/12* | (2006.01) |
| *B01J 23/62* | (2006.01) |
| *B01J 23/60* | (2006.01) |
| *B01J 31/02* | (2006.01) |
| *B01J 37/08* | (2006.01) |
| *B01J 21/18* | (2006.01) |
| *B01J 37/02* | (2006.01) |

(52) U.S. Cl.
CPC *B01J 23/62* (2013.01); *B01J 21/18* (2013.01); *B01J 23/60* (2013.01); *B01J 23/624* (2013.01); *B01J 31/0231* (2013.01); *B01J 37/0201* (2013.01); *B01J 37/08* (2013.01); *C07C 51/12* (2013.01); *C07C 67/36* (2013.01)

(58) Field of Classification Search
CPC .......... C07C 67/36; C07C 51/12; B01J 23/62; B01J 23/622
See application file for complete search history.

(56) References Cited

U.S. PATENT DOCUMENTS

| | | | |
|---|---|---|---|
| 3,689,533 A | 9/1972 | Schultz | |
| 3,717,670 A | 2/1973 | Schultz | |
| 3,772,380 A | 11/1973 | Paulik et al. | |
| 4,417,077 A | 11/1983 | Drago et al. | |
| 4,612,387 A | 9/1986 | Feitler | |
| 4,776,987 A | 10/1988 | Luft et al. | |
| 4,918,218 A | 4/1990 | Mueller et al. | |
| 5,185,462 A | 2/1993 | Evans et al. | |
| 5,218,140 A | 6/1993 | Wegman | |
| 5,258,549 A | 11/1993 | Pimblett | |
| 5,488,143 A | 1/1996 | Uhm et al. | |
| 5,510,524 A | 4/1996 | Garland et al. | |
| 5,696,284 A * | 12/1997 | Baker et al. | .............. 560/232 |
| 5,900,505 A * | 5/1999 | Tustin et al. | .............. 562/519 |
| 5,917,089 A | 6/1999 | Howard | |
| 6,137,000 A | 10/2000 | Zoeller et al. | |
| 6,177,380 B1 | 1/2001 | Zoeller et al. | |
| 6,353,132 B1 | 3/2002 | Zoeller et al. | |
| 6,355,595 B1 | 3/2002 | Zoeller et al. | |
| 6,355,837 B1 | 3/2002 | Zoeller et al. | |
| 6,458,995 B1 | 10/2002 | Cheung et al. | |
| 6,548,444 B2 | 4/2003 | Zoeller et al. | |
| 2006/0155144 A1 | 7/2006 | Haynes et al. | |
| 2008/0091046 A1 | 4/2008 | Smith | |
| 2010/0113827 A1 | 5/2010 | Wang | |

FOREIGN PATENT DOCUMENTS

| | | |
|---|---|---|
| EP | 0 461 802 A2 | 12/1991 |
| EP | 0 596 632 A1 | 5/1994 |
| EP | 0 643 034 A1 | 3/1995 |
| EP | 0 759 419 A1 | 2/1997 |
| WO | WO 2005/009939 A1 | 2/2005 |

OTHER PUBLICATIONS

Fujimoto, K. et al.; "Hydrogen Effects on Nickel-Catalyzed Vapor-Phase Methanol Carbonylation"; Journal of Catalysis; vol. 133, pp. 370-382; 1992.

Fujimoto, Kaoru et al; "Promotion Effect of Hydrogen on Vapor Phase Carbonylation of Methanol over Nickel on Active Carbon Catalyst"; Chemistry Letters; pp. 895-898; Jan. 1987.

Gelin, P. et al.; "Coordination chemistry of rhodium and iridium in constrained zeolite cavities: methanol carbonylation"; Pure & Appl. Chem.; vol. 60, No. 8; pp. 1315-1320; 1988.

Howard, M. J. et al.; "$C_1$ to acetyls: catalysis and process"; Catalysis Today; vol. 18; pp. 325-354; 1993.

Krzywicki, Andrzej and Marczewski, Marek; "Formation and Evolution of the Active Site for Methanol Carbonylation on Oxide Catalysts Containing $RhCl_3$"; Journal of Molecular Catalysis; vol. 6; pp. 431-440; Feb. 1979.

Liu, Tuan-Chi and Chiu, Shwu-Jer; "Promoting Effect of Tin on Ni/C Catalyst for Methanol Carbonylation"; Ind. Eng. Chem. Res.; vol. 33; pp. 488-492; 1994.

(Continued)

*Primary Examiner* — Paul A Zucker

(74) *Attorney, Agent, or Firm* — James Arnold, Jr.

(57) ABSTRACT

A solid catalyst comprising an effective amount of iridium and at least one second metal selected from gallium, zinc, indium and germanium associated with a solid support material is useful for vapor phase carbonylation to produce carboxylic acids and esters from alkyl alcohols, esters, ethers or ester-alcohol mixtures. The iridium and at least one second metal are deposited on a support material. In some embodiments of the invention, the catalyst is useful for vapor phase carbonylation.

19 Claims, 1 Drawing Sheet

(56) References Cited

OTHER PUBLICATIONS

Maneck, H. E. et al.; "Heterogeneous Carbonylation of Methanol on Rhodium Introduced into Faujasite-Type Zeolites"; Catalysis Today; vol. 3; pp. 421-429; 1988.

Webber, K. M. et al.; "Design and Synthesis of a Solid Bifunctional Polymer Catalyst for Methanol Carbonylation"; Journal of Molecular Catalysis; vol. 3; pp. 1-9; 1977/78.

Yagita, Hiroshi et al.; "Vapor-Phase Carbonylation of Methanol over Lead on Active Carbon Catalyst"; Catalysis Letters; vol. 2; pp. 145-148; 1989.

Notification of Transmittal of the International Search Report and the Written Opinion of the International Searching Authority, or the Declaration date of mailing Feb. 26, 2013 received in corresponding International Patent Application No. PCT/US12/70920.

* cited by examiner

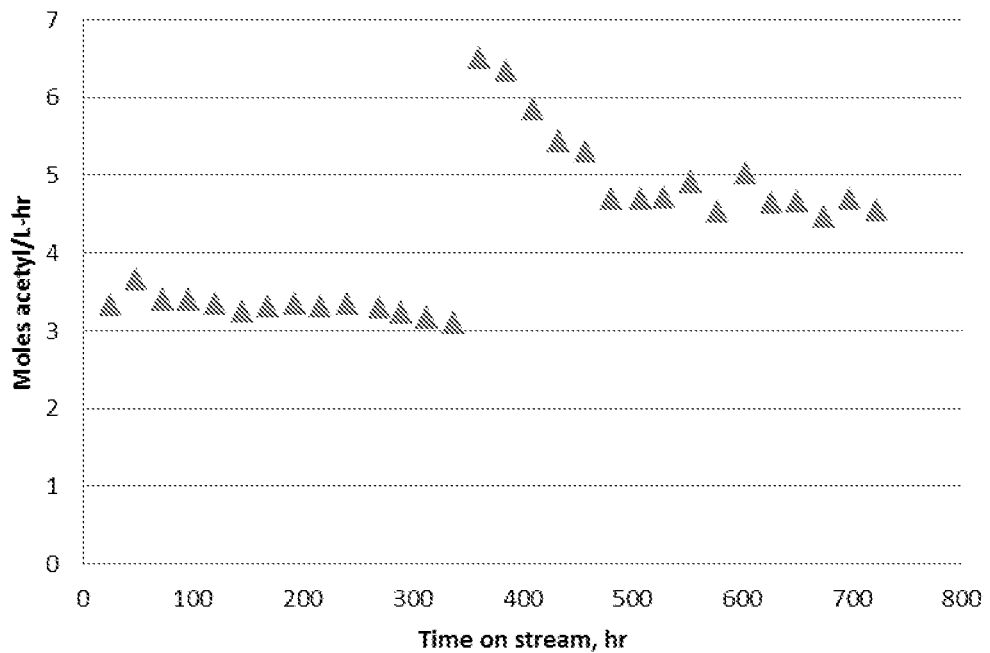

IRIDIUM CATALYSTS FOR CARBONYLATION

CROSS REFERENCE TO RELATED APPLICATION

This application claims the benefit of U.S. Provisional Application No. 61/580,818 filed on Dec. 28, 2011, the disclosure of which is incorporated herein by reference to the extent it does not contradict the disclosures herein.

FIELD OF THE INVENTION

The present invention relates to a solid phase catalyst and more particularly to a catalyst for the vapor phase carbonylation of alkyl alcohols, ethers and ester-alcohol mixtures to produce esters and carboxylic acids. More particularly, the present invention relates to a catalyst having an effective amount of iridium and at least one second metal selected from the group gallium, zinc, indium and germanium associated with a solid support material. The catalyst is particularly useful in the carbonylation of methanol.

BACKGROUND OF THE INVENTION

Lower carboxylic acids and esters such as acetic acid and methyl acetate have been known as industrial chemicals for many years. Acetic acid is used in the manufacture of a variety of intermediary and end-products. For example, an important derivative is vinyl acetate which can be used as monomer or co-monomer for a variety of polymers. Acetic acid itself is used as a solvent in the production of terephthalic acid, which is widely used in the container industry, and particularly in the formation of PET beverage containers.

There has been considerable research activity in the use of metal catalysts for the carbonylation of alkyl alcohols, such as methanol, and ethers to their corresponding carboxylic acids and esters, as illustrated in equations 1-3 below:

$$ROH + CO \rightarrow RCOOH \quad (1)$$

$$2ROH + CO \rightarrow RCOOR + water \quad (2)$$

$$ROR' + CO \rightarrow RCOOR \quad (3)$$

Carbonylation of methanol is typically carried out in the liquid phase with a catalyst. However, there is a continuing need for a catalyst which can be used in a vapor phase carbonylation process for the production of carboxylic acids and their esters and in which the catalyst is maintained in the solid phase.

SUMMARY OF THE INVENTION

Briefly, the present invention relates to solid supported catalysts for producing esters and carboxylic acids in a vapor phase carbonylation process, processes for making the catalyst compositions, and carbonylation processes that use such catalysts. Suitable reactants for contacting the solid catalyst includes alkyl alcohols, ethers and ester-alcohol mixtures. The catalyst includes an effective amount of iridium and at least one second metal selected from gallium, zinc, indium and germanium, wherein the iridium and at least one second metal are associated with a solid support material which, desirably, is inert to the carbonylation reaction.

The invention thus provides carbonylation catalysts containing an effective amount of iridium and at least one second metal selected from gallium, zinc, indium and germanium wherein the iridium and the at least one second metal are associated with a solid support material. The invention further carbonylation catalyst containing from about 0.01 weight percent to about 10 weight percent each of iridium and at least one second metal selected from gallium, zinc, indium and germanium wherein the iridium and at least one second metal are associated with a solid support material. In some embodiments, the solid support material is selected from carbon, activated carbon, pumice, alumina, silica, silica-alumina, magnesia, diatomaceous earth, bauxite, titania, zirconia, clay, magnesium silicate, silicon carbide, zeolites, ceramics and combinations thereof. In some embodiments, the solid support material contains activated carbon. In some embodiments, the molar ratio of the at least one second metal to iridium is from about 0.5:1 to about 5:1. In some embodiments, the catalyst includes from about 0.1 weight percent to about 3 weight percent each of the iridium and the at least one second metal. In some embodiments, the molar ratio of the at least one second metal to iridium is from about 0.1:1 to about 10:1. In some embodiments, the catalyst includes at least one vaporous halogen promoting component selected from hydrogen halides, gaseous hydrogen iodide, alkyl and aryl halides having up to 12 carbon atoms, iodine, bromine or chlorine, and mixtures of two or more of the foregoing. In some embodiments, the at least one vaporous halogen promoting component is selected from hydrogen iodide, methyl iodide, ethyl iodide, 1-iodopropane, 2-iodobutane, 1-iodobutane, hydrogen bromide, methyl bromide, ethyl bromide, benzyl iodide and combinations of two or more of the foregoing. In some embodiments, the at least one vaporous halogen promoting component is selected from hydrogen iodide, methyl iodide, hydrogen bromide, methyl bromide and combinations of two or more of the foregoing.

The invention further provides methods for producing at least one carboxylic acid, ester, or combination of carboxylic acid and ester mixtures from at least one reactant selected from alkyl alcohols, ethers, esters and combinations of two or more of the foregoing, which methods include contacting the at least one reactant with carbon monoxide in a reaction zone under vapor-phase carbonylation reaction conditions in the presence of a catalyst of the present invention, then recovering at least one carboxylic acid or ester from the reaction zone. In some embodiments, the reaction zone is maintained at a pressure of from about 0.1 to about 100 bar absolute and a temperature of from about 100° C. to about 350° C.

The invention further provides methods for preparing a solid supported catalyst composition useful for vapor phase carbonylation. The methods including: (a) providing a solid support material selected from carbon, activated carbon, pumice, alumina, silica, silica-alumina, magnesia, diatomaceous earth, bauxite, titania, zirconia, clays, magnesium silicate, silicon carbide, zeolites, ceramics and combinations of two or more of the foregoing; (b) contacting the support material with a solution containing iridium and at least one second metal selected from gallium, zinc, indium and germanium wherein the iridium and the at least one second metal are associated with the solid support material; and (c) drying the solid support material wherein from about 0.01 weight percent to about 10 weight percent of the iridium and at least one second metal are associated with the solid catalyst support material, wherein weight percent of each metal is determined as the weight of atoms of that particular metal based on the total weight of the solid supported catalytic material.

BRIEF DESCRIPTION OF THE DRAWING

The drawing of FIG. 1 is a plot of acetyl space time yield vs. time on stream of Example 13 herein demonstrating the longevity of the catalyst of the present invention.

DETAILED DESCRIPTION OF THE INVENTION

The catalyst of the present invention is particularly useful for the continuous production of carboxylic acids and esters by reacting alkyl alcohols, ethers and ester-alcohol mixtures in a vapor-phase carbonylation process. The catalyst includes an effective amount of iridium and at least one second metal selected from gallium, zinc, indium and germanium. The iridium and at least one second metal are associated with a solid support material. The catalyst is particularly useful in a vapor-phase carbonylation method for the continuous production of acetic acid, methyl acetate and combinations thereof.

As used herein, the term "effective amount" or "catalytically effective amount" means a measurable quantity of at least one substance, such as the primary metal, wherein the quantity or selectivity to make a targeted or desired product is at least 5 weight % greater in a given process than what would be produced under the same conditions without the substance. In some embodiments, the amount is from about 0.01 weight percent to about 10 weight percent each of iridium and at least one second metal selected from gallium, zinc, indium and germanium wherein the iridium and at least one second metal are associated with a solid support material. In some embodiments, the amount is from about 0.1 weight percent to about 3 weight percent each of the iridium and the at least one second metal.

As used herein, the term "associated with" means that one or more substances are deposited upon or joined with another material in such a manner that such substances are not readily removed under vapor-phase carbonylation reaction conditions.

Making the Catalyst

The compound or form of iridium used to prepare the catalyst generally is not critical, and the catalyst may be prepared from any of a wide variety of iridium containing compounds. Some examples include many combinations of halides, trivalent nitrogen, organic compounds of trivalent phosphorous, carbonyl compounds monoxide, hydrides, and 2,4-pentane-dione, either alone or in combination. Such materials are available commercially and may be used in the preparation of the catalysts utilized in the present invention. In addition, the oxides of iridium may be used if dissolved in the appropriate medium. In some embodiments, iridium is used as a salt of one of its chlorides, such as iridium trichloride or hydrated trichloride, hexacholoro-iridate and any of the various salts of hexachloro-iridate(IV). One skilled in the art will understand that use of the iridium complexes can be comparable on the basis of cost, solubility, and performance.

Similarly, the compound or form of the at least one second metal compound (gallium, zinc, indium, germanium or combinations of two or more of the foregoing) used to prepare the catalyst generally is not critical, and the catalyst may be prepared using any of a wide variety of compounds containing one or more of the second metals. A wide variety of compounds of these elements containing various combinations of halides, acetates, nitrates, cyclopentadiene, and 2,4-pentane-dione, either alone or in combination, are available commercially and may be used in the preparation of the catalysts utilized in the process of the present invention. In some embodiments, the form of the at least one second metal that may be used to prepare the catalyst of the present invention includes halides, oxides, acetylacetonate, nitrate, perchlorate, phosphide, sulfate and sulfide, either alone or in mixtures. In addition, the oxides of these materials may be used if dissolved in the appropriate medium. In some embodiments, the compound is in a form selected from acetates, nitrates, and their halides. In some embodiments, the compound used to provide the at least one second metal is a water soluble form of the metal(s). For example, many halides of second metals are generally commercially available and water soluble.

The solid support useful for acting as a carrier for the iridium and the at least one second metal contains a porous solid of such size that it can be employed in fixed or fluidized bed reactors. Typical support materials have a size of from about 400 mesh per inch to about 0.5 mesh per inch. The shape of the solid support is not particularly important and can be regular or irregular and include extrudates, rods, spheres, broken pieces and the like disposed within the reactor.

In some embodiments, the support is carbon, including activated carbon, having a high surface area. Activated carbon may be derived from several sources including, but not limited to, coal, peat having a density of from about 0.03 grams/cubic centimeter ($g/cm^3$) to about 2.25 $g/cm^3$. The carbon can have a surface area of from about 200 square meters/gram ($m^2/g$) to about 1200 $m^2/g$. Other solid support materials may be used, either alone or in combination, in accordance with the present invention include pumice, alumina, silica, silica-alumina, magnesia, diatomaceous earth, bauxite, titania, zirconia, clays, magnesium silicate, silicon carbide, zeolites, and ceramics.

In some embodiments, the amount of iridium and at least one second metal on the support (determined as metal) can independently vary from about 0.01 weight percent to about 10 weight percent each, as metal. In some embodiments, the amount of iridium and at least one second metal on the support is from about 0.1 weight percent to about 3 weight percent for each component. The weight percent or "weight %" of each metal is determined as the weight of atoms of that particular metal based on the total weight of the solid components of the catalytic material.

In some embodiments, the molar ratio of the at least one second metal to iridium in the catalytic material, is from about 0.1:1 to about 10:1. In some embodiments, the molar ratio of the at least one second metal to iridium is from about 0.5:1 to about 5:1.

Any effective means may be used to prepare the catalyst. A variety of methods are known in which the contacting method provides association between iridium, the at least one second metal and the selected support material. For example, the metal components may be dissolved or dispersed in a suitable solvent. The solid support material is then contacted and desirably impregnated with the iridium and at least one second metal containing solvent. Various methods of contacting the support material with the iridium and at least one second metal may be employed. For example, an iridium containing solvent can be admixed with a solvent containing the at least one second metal prior to impregnating the support material. Alternatively, the respective one the solvents can be impregnated or associated with the support material separately. In some embodiments, the support material is impregnated the support material with a first solvent followed a second solvent. In some embodiments, the support is dried prior to contacting the second solvent. In some embodiments, the at least one second metal component may be deposited on a previously prepared catalyst support having the iridium component already incorporated thereon. Similarly, the iridium and at least one second metal(s) may be associated with the support material in a variety of forms. For example, slurries of the iridium and at least one second metal can be poured over the support material. Alternatively, the support material may be immersed in excess solutions of the active components with the excess being subsequently removed, for example by using techniques known to those skilled in the art. The solvent or liquid is evaporated, i.e. the solid support is dried so that at least a portion of the iridium and at least one second metal is associated with the solid support. In some embodiments, drying temperatures can range from about 100° C. to about 600° C. One skilled in the art will understand that the drying time is dependent upon the temperature, humidity, and solvent. Generally, lower temperatures require longer heating periods to effectively evaporate the solvent from the solid support.

In some embodiments, the liquid used to deliver the iridium and at least one second metal in a form a solution, dispersion, or suspension is a liquid having a low boiling point, i.e., high vapor pressure at a temperature of from about 10° C. to about 140° C. Some examples of suitable solvents include carbon tetrachloride, benzene, acetone, methanol, ethanol, isopropanol, isobutanol, pentane, hexane, cyclohexane, heptane, toluene, pyridine, diethylamine, acetaldehyde, acetic acid, tetrahydrofuran and water.

Promoting Components

In some embodiments of the present invention, a catalytic system is used having a solid supported catalyst component as described above, and a vaporous halogen promoting component which can be catalytically active and which aids in the carbonylation process. The halogen promoter may be introduced at any suitable location, such as the catalyst preparation step or into carbonylation reactor under vapor-phase carbonylation reaction conditions with conjunction with the reactants. While not wanting to be bound by any theory, it is considered that as a result of contacting the active metal components with the halogen promoter the ultimate active species of the iridium and at least one second metal may exist as one or more coordination compounds or a halide thereof.

The halide component includes one or more of chlorine, bromine and/or iodine. In some embodiments, the halide component includes bromine and/or iodine, which are vaporous under vapor-phase carbonylation conditions of temperature and pressure. Some examples of suitable halides include: hydrogen halides such as hydrogen iodide and gaseous hydrogen iodide; and alkyl and aryl halides having up to 12 carbon atoms such as methyl iodide, ethyl iodide, 1-iodopropane, 2-iodobutane, 1-iodobutane, methyl bromide, ethyl bromide, and benzyl iodide. Desirably, the halide is a hydrogen halide or an alkyl halide having up to 6 carbon atoms. In some embodiments, the halide is selected from hydrogen iodide, methyl bromide and methyl iodide. In some embodiments, the halide is a molecular halide such as $I_2$, $Br_2$ or $Cl_2$.

Carbonylation Processes

In some embodiments of the present invention, a method for producing esters and carboxylic acids from reactants including alkyl alcohols, ethers, esters and ester-alcohol mixtures and carbon monoxide is provided including contacting the reactants in a reaction zone under vapor-phase carbonylation reaction conditions with the solid supported catalyst described above and recovering the ester or carboxylic acid from the reaction zone. In practice, a gaseous composition containing: at least one alkyl alcohol, ether, esters and ester-alcohol mixture, either alone or in combination; carbon monoxide; and a halide are fed to the reaction zone of a carbonylation reactor containing the iridium and at least one second metal supported catalyst described above. The reactor is maintained under vapor-phase carbonylation reaction conditions of temperature and pressure. For example, in some embodiments in which acetic acid is the desired product, the feedstock may contain methyl alcohol, dimethyl ether, methyl acetate, a methyl halide or any combination thereof. If it is desired to increase the proportion of acid produced, in some embodiments the ester may be recycled to the reactor together with water or introduced into a separate reactor with water to produce the acid in a separate zone.

As used herein, "vapor-phase carbonylation reaction conditions" means temperature and pressure conditions suitable to allow vapor-phase carbonylation reaction to occur. Vapor-phase carbonylation is operated at temperatures above the dew point of the product mixture, i.e., the temperature at which condensation occurs. However, since the dew point is a complex function of dilution (particularly with respect to non-condensable gases such as unreacted carbon monoxide, hydrogen, or inert diluent gas), product composition, and pressure, the process may still be operated over a wide range of temperatures, provided the temperature exceeds the dew point of the product effluent. In practice, this generally dictates a temperature range of from about 100° C. to about 500° C. In some embodiments, the temperatures are in the range of from about 100° C. to about 350° C. In some embodiments, the temperatures are in the range of from about 150° C. to about 275° C. Advantageously, operating in the vapor phase reduces the potential for catalyst dissolution, i.e., metal leaching from the catalyst support, which occurs in the known heterogeneous processes operating in the presence of liquid compounds.

As with temperature, the useful pressure range is limited by the dew point of the product mixture. However, provided that the reaction is operated at a temperature sufficient to prevent liquefaction of the product effluent, a wide range of pressures may be used, e.g., pressures in the range of from about 0.1 to about 100 bar absolute. In some embodiments, the process is carried out at a pressure in the range of from about 1 to about 50 bar absolute. In some embodiments, the process is carried out at a pressure in the range of from about 3 to about 30 bar absolute.

Suitable feedstocks for carbonylation include alkyl alcohols, ethers, esters-alcohol mixtures and, as more fully discussed below, esters, which may be carbonylated using the catalyst of the present invention. Non-limiting examples of feedstocks include alcohols and ethers in which an aliphatic carbon atom is directly bonded to an oxygen atom of either an alcohol hydroxyl group in the compound or an ether oxygen in the compound and may further include aromatic moieties. In some embodiments, the feedstock is one or more alkyl alcohols having from 1 to 10 carbon atoms. In some embodiments the feedstock is selected from alkyl alcohols having from 1 to 6 carbon atoms, alkane polyols having 2 to 6 carbon atoms, alkyl alkylene polyethers having 3 to 20 carbon atoms and alkoxyalkanols having from 3 to 10 carbon atoms and combinations of two or more of the foregoing. In some embodiments the feedstock is selected from alkyl alcohols having from 1 to 6 carbon atoms. In some embodiments the feedstock reactant is methanol. In some embodiments using methanol, the methanol is fed as methanol or it is supplied in the form of a combination of materials which generate methanol. Some examples of such materials include: (i) methyl acetate and water and (ii) dimethyl ether and water. During carbonylation, both methyl acetate and dimethyl ether are formed within the reactor and, unless methyl acetate is the desired product, they are recycled with water to the reactor where they are converted to acetic acid. Accordingly, in some embodiments the catalyst of the present invention is useful to produce a carboxylic acid from an ester feed material.

While the presence of water in the gaseous feed mixture is not essential when using methanol, the presence of some water may be used in some embodiments to suppress formation of methyl acetate and/or dimethyl ether. When using methanol to generate acetic acid, the molar ratio of water to methanol in some embodiments is from about 0:1 to about 10:1. The molar ratio of water to methanol in some embodiments is from about 0.1:1 to about 1:1. When using an alternative source of methanol such as methyl acetate or dimethyl ether, the amount of water fed usually is increased to account for the mole of water required for hydrolysis of the methanol alternative. Accordingly, when using either methyl acetate or dimethyl ether, the mole ratio of water to ester or ether in some embodiments is in the range of from about 1:1 to about 10:1, in some embodiments from about 1:1 to about 3:1. In the preparation of acetic acid, it is apparent that combinations of methanol, methyl ester, and/or dimethyl ether are equivalent, provided the appropriate amount of water is added to hydrolyze the ether or ester to provide the methanol reactant.

In some embodiments in which the catalyst is used in a vapor-phase carbonylation process to produce methyl acetate, no water is added and dimethyl ether is the feedstock. In some embodiments in which methanol is used as the feedstock in the preparation of methyl acetate, water may be removed.

The carbon monoxide can be a purified carbon monoxide or include other gases. The carbon monoxide need not be of a high purity and may contain from about 1% by volume to about 99% by volume carbon monoxide, in some embodiments in the range of from about 70% by volume to about 99% by volume carbon monoxide. The remainder of the gas mixture can include such gases as nitrogen, hydrogen, carbon dioxide, water, paraffinic hydrocarbons having from one to four carbon atoms, and combinations of two or more of the foregoing. Although hydrogen is not part of the reaction stoichiometry, hydrogen may be useful in maintaining optimal catalyst activity. In some embodiments, the ratio of carbon monoxide to hydrogen generally ranges from about 99:1 to about 2:1, but ranges with even higher hydrogen levels are also likely to be useful.

The amount of halide present to produce an effective carbonylation ranges from a molar ratio of from about 1:1 to about 10,000:1. In some embodiments the is from about 5:1 to about 1000:1. The foregoing molar ratios are based on methanol or methanol equivalents to halide.

In some embodiments of the invention, the vapor-phase carbonylation catalyst of the present invention may be used for making acetic acid, methyl acetate or a combination thereof. The process includes contacting a gaseous mixture containing methanol and carbon monoxide with the iridium/second metal catalyst described above in a carbonylation zone and recovering a gaseous product from the carbonylation zone.

The various aspects of the present invention can be further illustrated and described by the following Examples. It should be understood, however, that these Examples are included merely for purposes of illustration and are not intended to limit the scope of the invention, unless otherwise specifically indicated.

In the examples which follow all of the catalysts were prepared in a similar manner except as specified otherwise.

Catalyst 1

A catalyst in accordance with the present invention was prepared by dissolving 419 milligrams (mg) of iridium trichloride hydrate (53.2 weight % Ir) in 25 milliliters (ml) of distilled water to form a first solution. A second solution was prepared by dissolving 631 mg gallium iodide in 10 ml of concentrated hydrochloric acid. The first and second solutions were then combined and added to 20.0 grams (g) of 12×40 mesh activated carbon granules using a rotary evaporator. The mixture was heated under a water bath at a temperature of 60° C. and evacuated under 30 Torr until the granules were dry. The mixture was then transferred to a 106 cm long×25 mm (outer diameter) quartz tube containing a quartz wool support plug. The quartz tube was placed in a Lindberg electric furnace and heated in an upward flow of nitrogen at a flow rate of 100 standard cubic centimeters per minute. The tube was gradually heated from room temperatures to 300° C. over a 2 hour period, then held at 300° C. for 2 hours before cooling back to ambient temperature to obtain the final catalyst for methanol carbonylation. The catalyst weighed 18.13 grams after drying. The catalyst prepared in this manner, designated as Catalyst 1, had a nominal metal content of 1.23 weight % Ir and 0.54 weight % Ga, representing an Ir:Ga molar ratio of 1:1.21.

Catalyst 2

The same procedure as above was repeated except that the amount of gallium iodide dissolved into 10 ml of concentrated hydrochloric acid was 1.89 grams. The catalyst weighed 18.91 grams after drying. The catalyst prepared in this manner, designated as Catalyst 2, had a nominal metal content of 1.18 weight % Ir and 1.55 weight % Ga, representing, an Ir:Ga molar ratio of 1:3.63.

Catalyst 3

The same procedure to prepare Catalyst 1 above was repeated except that the amount of gallium iodide dissolved into 10 ml of concentrated hydrochloric acid was 3.10 grams. The catalyst weighed 21.03 grams after drying. The catalyst prepared in this manner, designated as Catalyst 3, had a nominal metal content of 1.06 wt. % Ir and 2.28 wt. % Ga, representing, an Ir:Ga molar ratio of 1:5.92.

Catalyst 4

A catalyst in accordance with the present invention was prepared by dissolving 418 milligrams (mg) of iridium trichloride hydrate (53.2 weight % Ir) in 25 milliliters (ml) of distilled water to form a first solution. A second solution was prepared by dissolving 449 mg zinc iodide in 10 ml of concentrated hydrochloric acid. The first and second solutions were then combined and added to 20.0 grams (g) of 12×40 mesh activated carbon granules using a rotary evaporator. The mixture was heated under a water bath at a temperature of 60° C. and evacuated under 30 Torr until the granules were dry. The mixture was then transferred to a 106 cm long×25 mm (outer diameter) quartz tube containing a quartz wool support plug. The quartz tube was placed in a Lindberg electric furnace and heated to 300° C. over a 2 hour period in an upward flow of nitrogen a flow rate of 100 standard cubic centimeters per minute and held at 300° C. for 2 hours before cooling back to ambient temperature to obtain the final catalyst for methanol carbonylation. The catalyst weighed 18.46 grams after drying. The catalyst prepared in this manner, designated as Catalyst 4, had a nominal metal content of 1.21 weight % Ir and 0.50 weight % Zn, representing, an Ir:Zn molar ratio of 1:1.21.

Catalyst 5

The same procedure to prepare Catalyst 4 above was repeated except that the amount of zinc iodide dissolved into 10 ml of concentrated hydrochloric acid was 1.344 grams. The catalyst weighed 19.33 grams after drying. The catalyst prepared in this manner, designated as Catalyst 5, had a nominal metal content of 1.15 weight % Ir and 1.42 weight % Zn, representing, an Ir:Zn molar ratio of 1:3.63.

Catalyst 6

The same procedure to prepare Catalyst 4 above was repeated except that the amount of zinc iodide dissolved into 10 ml of concentrated hydrochloric acid was 2.24 grams. The catalyst weighed 19.86 grams after drying. The catalyst prepared in this manner, designated as Catalyst 6, had a nominal metal content of 1.12 weight % Ir and 2.31 weight % Zn, representing, an Ir:Zn molar ratio of 1:6.05.

Catalyst 7

A catalyst in accordance with the present invention was prepared by dissolving 418 milligrams (mg) of iridium trichloride hydrate (53.2 weight % Ir) in 25 milliliters (ml) of distilled water to form a first solution. A second solution was prepared by dissolving 695 mg indium iodide in 10 ml of concentrated hydrochloric acid. The first and second solutions were then combined and added to 20.0 grams (g) of 12×40 mesh activated carbon granules using a rotary evaporator. The mixture was heated under a water bath at a temperature of 60° C. and evacuated under 30 Torr until the granules were dry. The mixture was then transferred to a 106 cm long×25 mm (outer diameter) quartz tube containing a quartz wool support plug. The quartz tube was placed in a Lindberg electric furnace and heated to 300° C. over a 2 hour period in an upward flow of nitrogen a flow rate of 100 standard cubic centimeters per minute and held at 300° C. for 2 hours before cooling back to ambient temperature to obtain the final catalyst for methanol carbonylation. The catalyst weighed 19.15 grams after drying. The catalyst prepared in this manner, designated as Catalyst 7, had a nominal metal content of 1.16 weight % Ir and 0.84 weight % In, representing, an Ir:In molar ratio of 1:1.21.

Catalyst 8

The same procedure to prepare Catalyst 7 above was repeated except that the amount of indium iodide dissolved into 10 ml of concentrated hydrochloric acid was 2.085 grams. The catalyst weighed 20.46 grams after drying. The catalyst prepared in this manner, designated as Catalyst 8, had a nominal metal content of 1.09 weight % Ir and 2.36 weight % In, representing, an Ir:In molar ratio of 1:3.63.

Catalyst 9

The same procedure to prepare Catalyst 7 above was repeated except that the amount of indium iodide dissolved into 10 ml of concentrated hydrochloric acid was 3.475 grams. The catalyst weighed 21.92 grams after drying. The catalyst prepared in this manner, designated as Catalyst 9, had a nominal metal content of 1.02 weight % Ir and 3.67 weight % In, representing, an Ir:In molar ratio of 1:6.05.

Catalyst 10

A catalyst in accordance with the present invention was prepared by dissolving 418 milligrams (mg) of iridium trichloride hydrate (53.2 weight % Ir) in 25 milliliters (ml) of distilled water to form a first solution. A second solution was prepared by dissolving 2.438 grams of germanium iodide in 10 ml of concentrated hydrochloric acid. The first and second solutions were then combined and added to 20.0 grams (g) of 12×40 mesh activated carbon granules using a rotary evaporator. The mixture was heated under a water bath at a temperature of 60° C. and evacuated under 30 Torr until the granules were dry. The mixture was then transferred to a 106 cm long×25 mm (outer diameter) quartz tube containing a quartz wool support plug. The quartz tube was placed in a Lindberg electric furnace and heated to 300° C. over a 2 hour period in an upward flow of nitrogen a flow rate of 100 standard cubic centimeters per minute and held at 300° C. for 2 hours before cooling back to ambient temperature to obtain the final catalyst for methanol carbonylation. The catalyst weighed 20.83 grams after drying. The catalyst prepared in this manner, designated as Catalyst 10, had a nominal metal content of 1.07 weight % Ir and 1.47 weight % Ge, representing, an Ir:Ge molar ratio of 1:3.62.

Comparative Catalyst 1

A catalyst was prepared by dissolving 418 milligrams (mg) of iridium trichloride hydrate (53.2 weight % Ir) in 25 milliliters (ml) of distilled water and 10 ml of concentrated hydrochloric acid to form a solution. The solution was then added to 20.0 grams (g) of 12×40 mesh activated carbon granules using a rotary evaporator. The mixture was heated under a water bath at a temperature of 60° C. and evacuated under 30 Torr until the granules were dry. The mixture was then transferred to a 106 cm long×25 mm (outer diameter) quartz tube containing a quartz wool support plug. The quartz tube was placed in a Lindberg electric furnace and heated to 300° C. over a 2 hour period in an upward flow of nitrogen a flow rate of 100 standard cubic centimeters per minute and held at 300° C. for 2 hours before cooling back to ambient temperature to obtain the final catalyst for methanol carbonylation. The catalyst prepared in this manner had a metal content of approximately one (1) weight % Ir based on the total weight of the supported catalyst.

Comparative Catalyst 2

A catalyst in accordance with the present invention was prepared by dissolving 418 milligrams (mg) of iridium trichloride hydrate (53.2 weight % Ir) in 25 milliliters (ml) of distilled water to form a first solution. A second solution was prepared by dissolving 1.099 g ruthenium iodide hydrate ($RuCl_3 \cdot 3H_2O$) in 10 ml of concentrated hydrochloric acid. The first and second solutions were then combined and added to 20.0 grams (g) of 12×40 mesh activated carbon granules using a rotary evaporator. The mixture was heated under a water bath at a temperature of 60° C. and evacuated under 30 Torr until the granules were dry. The mixture was then transferred to a 106 cm long×25 mm (outer diameter) quartz tube containing a quartz wool support plug. The quartz tube was placed in a Lindberg electric furnace and heated to 300° C. over a 2 hour period in an upward flow of nitrogen a flow rate of 100 standard cubic centimeters per minute and held at 300° C. for 2 hours before cooling back to ambient temperature to obtain the final catalyst for methanol carbonylation. The catalyst weighed 18.79 grams after drying. The catalyst prepared in this manner had a nominal metal content of 1.19 weight % Ir and 2.26 weight % Ru, representing, an Ir:Ru molar ratio of 1:3.63.

Carbonylation of Methanol

In the examples which follow, the reactor included a clean Hastelloy C alloy tubing. Reactants entered the base of the reactor via an inside diameter (I.D.) of 0.374 of an inch. The portion above the inlet tube expanded as a conical collar piece into a cylindrical section having an I.D. of 0.625 of an inch and an overall length of 2.00 inches. The top 0.38 of an inch was machined to a diameter of 0.750 of an inch. The machined portion of the collar had an I.D. of 0.735 of an inch. A 5 micron metal filter acted as a gas dispersion device and a support for the catalyst. The filter and collar were welded to a 6.25 inch long×0.750 inch I.D. Hastelloy C alloy reaction tube. The reaction tube was welded to an expansion zone having a conical shape and an outer diameter of 1.50 inches, then continuing in a cylindrical cross-section for another 1.83 inches, then decreasing at a 45 degree angle and welded to a 4.50 inch long×0.375 inch outside diameter (O.D.) loading and sensing tube. The vertical loading and sensing tube contained a 0.375 inch O.D. pressure transducer side arm located 2.0 inches above the expanded zone and positioned 45 degrees from vertical from the loading and sensing tube. Vapor product was removed from the expanded zone through a 0.250 inch O.D. product removal line connected approximately half the vertical distance of the expanded zone. The product removal line exited the reactor horizontally and then bent downward.

Metered gas flows were maintained by Brooks 5850 Series E mass flow controllers interfaced with a Camile™ 3300 Process Monitoring and Control System. Temperature control was also provided by the Camile. 3300 Process Monitoring and Control System. Liquid feed was provided by an Alltech 301 HPLC pump. Liquid and gas feeds were vaporized by feeding to a heated Hastelloy C alloy vaporizer maintained at 150° C. and transported in the vapor phase through a transfer line at 150° C. to the base of the reactor inlet tube. Heat to the reactor was provided by three separate split aluminum blocks with each split aluminum block surrounded by band heaters. Each split aluminum block heating unit had its own temperature control provided by the Camile™ 3300 Process Monitoring and Control System. The bottom heater provided heat to the reactor inlet tube and collar piece. The central heater provided heat to the reaction tube section. The top heater provided heat to the expansion zone.

The end of the product removal line was connected to a 60 micron filter attached to a Hastelloy C alloy condenser, which was attached to a Hastelloy C alloy product collection tank with a working capacity of one liter. The pressure was maintained using a Tescom Model 44-2300 back pressure regulator (BPR) attached to a vent line on the top of product collection tank. Liquid samples were collected from a valve at the base of the liquid collection tank. The carbonylation products were weighed and analyzed by gas chromatography using a Hewlett Packard Model 6890 gas chromatograph fitted with a 30 meter×0.25 millimeter DB_FFAP capillary column (0.25 micron film thickness) programmed at 40° C. for 5 minutes, 25° C. per minute to 240° C. and holding at 240° C. for 1 minute using a thermal conductivity detector held at 250° C. (injector temperature=250° C.). Mixtures were prepared for gas chromatographic analysis by adding 5 ml tetrahydrofuran solution containing 2 wt % decane internal standard to an accurately weighed sample of the product mixture.

The vent gas samples were collected using either a small gas bomb before the BPR or a gas bag after BPR and the gas flow rate was measured after the BPR using a Bios flow meter with an average over five measurements. The gas analysis was done using a micro-GC with two modules. The module A is molecular sieve 10 m×320 μm×12 μm and module B is Plot U 8 m×320 μm×12 μm. The injection and column temperature of module A are both 100° C. The injection temperature of module B is 100° C. while the column temperature is 65° C.

The reactor was loaded with 10 ml of catalyst made above through the top of the reactor. The reactor was then pressurized to 200 psig with carbon monoxide (150 standard cubic centimeters per minute, SCCM). Then the vaporizer was set for 220° C. and the three reactor heaters were set for 190° C. with CO flowing at 150 SCCM through the base of the reactor. After the reactor temperature had stabilized at 190° C. at 200 psig, a solution containing methanol and methyl iodide in a weight ratio of 70 methanol/30 methyl iodide was fed to the reactor system at 0.11 ml/minute while maintaining the carbon monoxide flow at 150 SCCM. The experimental conditions were varied for each catalyst as shown in each example.

In the following examples "Rx temp" is the reactor temperature; "Liquid feed rate" is the reactant methanol feed rate; "MeOH:MeI" is the molar ratio of methanol to methyl iodide in the feed; "CO:MeOH" is the molar ratio of carbon monoxide to methanol in the feed. MeOH conversion is defined as (methanol from feed minus methanol remaining)/(methanol from feed)×100%. "Acetyl STY" is the rate of acetyl production, which is the amount (moles) of methyl acetate and acetic acid produced per liter of catalyst per hour. CO conversion is defined as (CO from feed-CO remaining)/(CO from feed)×100%. "Methane produced vs. acetyl produced" is defined as the methane amount (moles)/total amount (moles) of methyl acetate and acetic acid. "Molar ratio of HOAc:MeOAc" is defined as molar ratio of acetic acid to methyl acetate.

Example 1

The reaction conditions in which Catalyst 1 (Ir:Ga molar ratio of 1:1.21) was used are set forth in Tables 1A (feed) and 1B (product) below.

TABLE 1A

| (Feed) | | | | |
|---|---|---|---|---|
| Run No. | Rx temp (° C.) | liquid feed rate (ml/min) | MeOH:MeI molar ratio | CO:MeOH molar ratio |
| A | 190 | 0.11 | 10 | 2.83 |
| B | 210 | 0.11 | 10 | 2.83 |
| C | 190 | 0.11 | 25 | 2.62 |
| D | 190 | 0.11 | 25 | 1.22 |
| E | 190 | 0.22 | 25 | 1.31 |

TABLE 1B

| (Product) | | | | |
|---|---|---|---|---|
| | % Conversion | | | methane produce vs |
| Run No. | % MeOH | % CO | Acetyl STY moles/L-hr | acetyl produced | HOAc:MeOAc molar ratio |
| A | 97.32 | 34 | 9.33 | 0.02 | 1.48 |
| B | 99.72 | 17 | 9.97 | 0.05 | 3.90 |
| C | 98.74 | 26 | 11.64 | 0.08 | 2.05 |
| D | 99.69 | 51 | 12.13 | 0.02 | 3.46 |
| E | 99.61 | 66 | 22.10 | 0.12 | 3.13 |

Example 2

The reaction conditions in which Catalyst 2 (Ir:Ga molar ratio of 1:3.63) was used are set forth in Tables 2A (feed) and 2B (product) below.

TABLE 2A

| (Feed) | | | | |
|---|---|---|---|---|
| Run No | Rx temp (° C.) | liquid feed rate (ml/min) | MeOH:MeI molar ratio | CO:MeOH molar ratio |
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |
| E | 190 | 0.11 | 25 | 1.22 |

TABLE 2B

| | (Product) | | | | |
|---|---|---|---|---|---|
| | % Conversion | | | methane produce vs | |
| Run No. | % MeOH | % CO | Acetyl STY moles/L-hr | acetyl produced | HOAc:MeOAc molar ratio |
| A | 100 | 22 | 12.47 | 0.07 | 14.40 |
| B | 100 | 55 | 23.75 | 0.04 | 8.25 |
| C | 100 | 28 | 12.64 | 0.04 | 26.43 |
| D | 100 | 27 | 12.71 | 0.07 | 10.26 |
| E | 100 | 70 | 12.41 | 0.01 | 9.40 |

Example 3

The reaction conditions in which Catalyst 3 (Ir:Ga molar ratio of 1:5.92) was used are set forth in Tables 3A (feed) and 3B (product) below.

TABLE 3A

| | (Feed) | | | |
|---|---|---|---|---|
| Run No. | Rx temp (° C.) | liquid feed rate (ml/min) | MeOH:MeI molar ratio | CO:MeOH molar ratio |
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |
| E | 190 | 0.11 | 25 | 1.22 |
| F | 190 | 0.22 | 25 | 1.31 |

TABLE 3B

| | (Product) | | | | |
|---|---|---|---|---|---|
| | % Conversion | | | methane produce vs | |
| Run No. | % MeOH | % CO | Acetyl STY moles/L-hr | acetyl produced | HOAc:MeOAc molar ratio |
| A | 100 | 22 | 13.18 | 0.08 | 105.66 |
| B | 100 | 61 | 24.31 | 0.05 | 18.04 |
| C | 100 | 35 | 12.84 | 0.10 | 48.97 |
| D | 100 | 31 | 12.91 | 0.08 | 15.95 |
| E | 100 | 63 | 12.85 | 0.03 | 8.39 |
| F | 99.68 | 56 | 22.31 | 0.09 | 4.43 |

Example 4

The reaction conditions in which Catalyst 4 (Ir:Zn molar ratio of 1:1.21) was used are set forth in Tables 4A (feed) and 4B (product) below.

TABLE 4A

| | (Feed) | | | |
|---|---|---|---|---|
| Run No. | Rx temp (° C.) | liquid feed rate (ml/min) | MeOH:MeI molar ratio | CO:MeOH molar ratio |
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |

TABLE 4A-continued

| | (Feed) | | | |
|---|---|---|---|---|
| Run No. | Rx temp (° C.) | liquid feed rate (ml/min) | MeOH:MeI molar ratio | CO:MeOH molar ratio |
| E | 190 | 0.11 | 25 | 1.22 |
| F | 190 | 0.22 | 25 | 1.31 |

TABLE 4B

| | (Product) | | | | |
|---|---|---|---|---|---|
| | % Conversion | | | methane produce vs | |
| Run No. | % MeOH | % CO | Acetyl STY moles/L-hr | acetyl produced | HOAc:MeOAc molar ratio |
| A | 99.58 | 32 | 10.04 | 0.08 | 3.27 |
| B | 99.36 | 53 | 18.21 | 0.14 | 2.61 |
| C | 99.53 | 69 | 11.52 | 0.11 | 4.61 |
| D | 99.75 | 36 | 11.93 | 0.09 | 3.90 |
| E | 98.93 | 58 | 10.37 | 0.04 | 3.08 |
| F | 97.58 | 89 | 17.13 | 0.12 | 1.99 |

Example 5

The reaction conditions in which Catalyst 5 (Ir:Zn molar ratio of 1:3.63) was used are set forth in Tables 5A (feed) and 5B (product) below.

TABLE 5A

| | (Feed) | | | |
|---|---|---|---|---|
| Run No. | Rx temp (° C.) | liquid feed rate (ml/min) | MeOH:MeI molar ratio | CO:MeOH molar ratio |
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |
| E | 190 | 0.11 | 25 | 1.22 |
| F | 190 | 0.22 | 25 | 1.31 |

TABLE 5B

| | (Product) | | | | |
|---|---|---|---|---|---|
| | % Conversion | | | methane produce vs | |
| Run No. | % MeOH | % CO | Acetyl STY moles/L-hr | acetyl produced | HOAc:MeOAc molar ratio |
| A | 100.00 | 36 | 12.59 | 0.03 | 15.23 |
| B | 100.00 | 62 | 22.10 | 0.05 | 5.13 |
| C | 100.00 | 38 | 13.43 | 0.06 | 18.58 |
| D | 99.97 | 38 | 13.56 | 0.07 | 9.24 |
| E | 100.00 | 71 | 12.62 | 0.00 | 5.95 |
| F | 100.00 | 64 | 24.72 | 0.07 | 7.20 |

Example 6

The reaction conditions in which Catalyst 6 (Ir:Zn molar ratio of 1:6.05) was used are set forth in Tables 6A (feed) and 6B (product) below.

TABLE 6A (Feed)

| Run No. | Rx temp (° C.) | liquid feed rate (ml/min) | MeOH:MeI molar ratio | CO:MeOH molar ratio |
|---|---|---|---|---|
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |
| E | 190 | 0.11 | 25 | 1.22 |
| F | 190 | 0.22 | 25 | 1.31 |

TABLE 6B (Product)

| Run No. | % Conversion % MeOH | % CO | Acetyl STY moles/L-hr | methane produce vs acetyl produced | HOAc:MeOAc molar ratio |
|---|---|---|---|---|---|
| A | 100.00 | 35 | 12.62 | 0.02 | 51.28 |
| B | 100.00 | 62 | 22.27 | 0.06 | 17.55 |
| C | 100.00 | 39 | 12.92 | 0.11 | 65.05 |
| D | 100.00 | 40 | 13.93 | 0.05 | 36.95 |
| E | 99.51 | 48 | 11.89 | 0.05 | 3.05 |
| F | 97.83 | 33 | 20.22 | 0.14 | 1.34 |

Example 7

The reaction conditions in which Catalyst 7 (Ir:In molar ratio of 1:1.21) was used are set forth in Tables 7A (feed) and 7B (product) below.

TABLE 7A (Feed)

| Run No. | Rx temp (° C.) | liquid feed rate (ml/min) | MeOH:MeI molar ratio | CO:MeOH molar ratio |
|---|---|---|---|---|
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |
| E | 190 | 0.11 | 25 | 1.22 |
| F | 190 | 0.22 | 25 | 1.31 |

TABLE 7B (Product)

| Run No. | % Conversion % MeOH | % CO | Acetyl STY moles/L-hr | methane produce vs acetyl produced | HOAc:MeOAc molar ratio |
|---|---|---|---|---|---|
| A | 99.28 | 28 | 9.89 | 0.01 | 2.30 |
| B | 98.22 | 48 | 17.54 | 0.02 | 1.01 |
| C | 99.60 | 33 | 11.06 | 0.03 | 3.18 |
| D | 99.20 | 24 | 9.89 | 0.02 | 1.78 |
| E | 99.47 | 53 | 11.36 | 0.01 | 2.64 |
| F | 99.09 | 44 | 21.78 | 0.05 | 1.77 |

Example 8

The reaction conditions in which Catalyst 8 (Ir:In molar ratio of 1:3.63) was used are set forth in Tables 8A (feed) and 8B (product) below.

TABLE 8A (Feed)

| Run No. | Rx temp (° C.) | liquid feed rate (ml/min) | MeOH:MeI molar ratio | CO:MeOH molar ratio |
|---|---|---|---|---|
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |
| E | 190 | 0.11 | 25 | 1.22 |
| F | 190 | 0.22 | 25 | 1.31 |

TABLE 8B (Product)

| Run No. | % Conversion % MeOH | % CO | Acetyl STY moles/L-hr | methane produce vs acetyl produced | HOAc:MeOAc molar ratio |
|---|---|---|---|---|---|
| A | 100.00 | 40 | 13.31 | 0.03 | 170.53 |
| B | 100.00 | 65 | 25.35 | 0.03 | 18.66 |
| C | 100.00 | 33 | 11.87 | 0.11 | 20.66 |
| D | 99.52 | 25 | 8.54 | 0.08 | 3.07 |
| E | 99.15 | 56 | 9.42 | 0.01 | 2.51 |
| F | 92.45 | 50 | 17.81 | 0.00 | 1.11 |

Example 9

The reaction conditions in which Catalyst 9 (Ir:In molar ratio of 1:6.05) was used are set forth in Tables 9A (feed) and 9B (product) below.

TABLE 9A (Feed)

| Run No. | Rx temp (° C.) | liquid feed rate (ml/min) | MeOH:MeI molar ratio | CO:MeOH molar ratio |
|---|---|---|---|---|
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |

TABLE 9A-continued

| | | (Feed) | | |
|---|---|---|---|---|
| Run No. | Rx temp (° C.) | liquid feed rate (ml/min) | MeOH:MeI molar ratio | CO:MeOH molar ratio |
| E | 190 | 0.11 | 25 | 1.22 |
| F | 190 | 0.22 | 25 | 1.31 |

TABLE 9B

| | (Product) | | | |
|---|---|---|---|---|
| Run No. | % Conversion % MeOH | % CO | Acetyl STY moles/L-hr | methane produce vs acetyl produced | HOAc:MeOAc molar ratio |

| Run No. | % MeOH | % CO | Acetyl STY moles/L-hr | methane produce vs acetyl produced | HOAc:MeOAc molar ratio |
|---|---|---|---|---|---|
| A | 100.00 | 49 | 13.47 | 0.03 | 169.93 |
| B | 99.57 | 42 | 22.88 | 0.07 | 5.56 |
| C | 98.89 | 31 | 8.50 | 0.14 | 3.10 |
| D | 71.81 | 20 | 4.03 | 0.05 | 0.71 |
| E | 80.77 | 16 | 4.07 | 0.03 | 0.50 |
| F | 61.56 | 11 | 6.08 | 0.07 | 0.29 |

Example 10

The reaction conditions in which Catalyst 10 (Ir:Ge molar ratio of 1:3.62) was used are set forth in Tables 10A (feed) and 10B (product) below.

TABLE 10A

| | | (Feed) | | |
|---|---|---|---|---|
| Run No. | Rx temp (° C.) | liquid feed rate (ml/min) | MeOH:MeI molar ratio | CO:MeOH molar ratio |
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |
| E | 190 | 0.11 | 25 | 1.22 |
| F | 190 | 0.22 | 25 | 1.31 |

TABLE 10B

| Run No. | % MeOH | % CO | Acetyl STY moles/L-hr | methane produce vs acetyl produced | HOAc:MeOAc molar ratio |
|---|---|---|---|---|---|
| A | 96.61 | 26 | 8.92 | 0.02 | 0.89 |
| B | 91.07 | 36 | 15.33 | 0.08 | 0.72 |
| C | 98.29 | 14 | 9.46 | 0.02 | 1.42 |
| D | 96.43 | 21 | 9.60 | 0.03 | 0.91 |
| E | 95.00 | 45 | 9.08 | 0.03 | 0.77 |
| F | 82.20 | 27 | 14.53 | 0.11 | 0.43 |

Example 11 (Comparative)

Comparative catalyst Ir/C was utilized in the carbonylation of methanol according to the above-described procedure. The reaction conditions in which comparative catalyst Ir/C was used are set forth in Table 11. Table 11 shows that the reaction rate for catalyst of the present invention are significantly more than the reaction rates of the Ir/C catalyst.

TABLE 11A

| | | (Feed) | | |
|---|---|---|---|---|
| Run No. | Rx temp (° C.) | liquid feed rate (ml/min) | MeOH:MeI molar ratio | CO:MeOH molar ratio |
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |
| E | 190 | 0.11 | 25 | 1.22 |
| F | 190 | 0.22 | 25 | 1.31 |
| G | 190 | 0.11 | 10 | 2.83 |

TABLE 11B

| Run No. | % MeOH | % CO | Acetyl STY moles/L-hr | methane produce vs acetyl produced | HOAc:MeOAc molar ratio |
|---|---|---|---|---|---|
| A | 95.58 | 14 | 8.05 | 0.02 | 0.77 |
| B | 88.03 | 29 | 14.01 | 0.07 | 0.49 |
| C | 95.56 | 17 | 8.51 | 0.06 | 1.01 |
| D | 92.73 | 18 | 8.82 | 0.05 | 0.99 |
| E | 85.77 | 30 | 7.00 | 0.03 | 0.32 |
| F | 84.26 | 35 | 13.78 | 0.28 | 0.46 |
| G | 59.71 | 8 | 3.97 | 0.27 | 0.15 |

Example 12 (Comparative)

Comparative catalyst Ir/Ru/C (molar ratio of Ir:Ru 1:3.63) was utilized in the carbonylation of methanol according to the above-described procedure. The reaction conditions in which comparative catalyst Ir/Ru/C was used are set forth in Table 12. Table 12 shows that the rate of reaction of the catalyst of the present invention is significantly more than the reaction rates of the Ir/Ru/C catalyst.

TABLE 12A

| | | (Feed) | | |
|---|---|---|---|---|
| Run No. | Rx temp (° C.) | liquid feed rate (ml/min) | MeOH:MeI molar ratio | CO:MeOH molar ratio |
| A | 190 | 0.11 | 10 | 2.83 |
| B | 190 | 0.22 | 10 | 1.42 |
| C | 210 | 0.11 | 10 | 2.83 |
| D | 190 | 0.11 | 25 | 2.62 |
| E | 190 | 0.11 | 25 | 1.22 |
| F | 190 | 0.22 | 25 | 1.31 |
| G | 190 | 0.11 | 10 | 2.83 |

TABLE 12B

| | (Product) | | | | |
|---|---|---|---|---|---|
| Run No. | % Conversion % MeOH | % CO | Acetyl STY moles/L-hr | methane produce vs acetyl produced | HOAc:MeOAc molar ratio |
| A | 99.76 | 16 | 11.73 | 0.01 | 4.88 |
| B | 98.66 | 27 | 17.64 | 0.02 | 1.64 |
| C | 99.86 | 19 | 8.56 | 0.04 | 5.80 |
| D | 99.81 | 13 | 10.07 | 0.02 | 3.81 |
| E | 99.65 | 35 | 10.34 | 0.01 | 3.03 |
| F | 98.58 | 36 | 18.33 | 0.04 | 1.43 |
| G | 99.92 | 15 | 8.62 | 0.02 | 5.81 |

Example 13

Example 13 demonstrates the longevity of the catalyst of the present invention. Four parallel fixed bed reactors were designed for catalyst life time study. Each reactor system includes a gas feed manifold, a feed pre-heater, a reactor, a condenser for separation of liquid and gas product, and operates independently. They were designed to operate at a maximum temperature of 400° C. and a maximum pressure of 450 psig. The whole reactor system is controlled by a distributive control system. This system controls the temperature, feed rates, gases, and other parameters on the system as whole.

The reactor was constructed entirely of Hastelloy C alloy. Reactants entered the base of the reactor via a 0.375 inch (9.5 mm) outer diameter (O.D.) inlet tube having a wall thickness of 0.035 inch. Metered gas flows were maintained by Brooks 5850 Series E mass flow controllers interfaced with a distributive control system. Temperature control was also provided by the distributive control system. Liquid feed was provided by an Alltech 301 HPLC pump. Liquid and gas feeds were vaporized by feeding to a heated Hastelloy C alloy vaporizer maintained at 190° C. and transported in the vapor phase through a transfer line at 180° C. to the base of the reactor inlet tube. Heat to the reactor was provided by the aluminum block surrounded by the band heater. The aluminum block heating unit had its own temperature control provided by the distributive control system. The portion of the product removal line above the reactor was heat traced with heat tape at 180° C.

The end of the product removal line was connected to a 60 micron filter attached to a Hastelloy C alloy condenser, which was attached to a Hastelloy C alloy product collection tank with a working capacity of 1 liter. The pressure was maintained using a backpressure regulator attached to a vent line on the top of product collection tank. Liquid samples were collected from a valve at the base of the liquid collection tank. The carbonylation products were weighed and analyzed by gas chromatography as in previous examples.

One of the parallel reactors was loaded with 2 ml of catalyst through the top of the reactor. The reactor was then pressurized to 200 psig with carbon monoxide (150 SCCM). Then the vaporizer was set for 190° C. and the reactor heater was set for 190° C. with CO flowing at 150 SCCM through the base of the reactor. After the reactor temperature had stabilized at 190° C. at 200 psig, a solution containing 1 weight % methyl iodide in methanol was fed to the reactor system at 0.02 ml/minute while maintaining the carbon monoxide flow at 30 SCCM. One sample per day was taken. The life time of Ir—Ga/C catalyst with 0.75 weight % Ir and a molar ratio of Ir:Ga of 1.3 was examined for 700 hours. The acetyl space time yield vs. time on stream was shown in the FIG. 1. The catalyst was tested at 200° C. in the first 350 hours and then tested at 240° C. for the rest time on stream.

The preferred forms of the invention described above are to be used as illustration only, and should not be used in a limiting sense to interpret the scope of the present invention. Obvious modifications to the exemplary one embodiment, set forth above, could be readily made by those skilled in the art without departing from the spirit of the present invention.

We claim:

1. A method for producing at least one carboxylic acid, ester, or combination of carboxylic acid and ester mixtures from at least one reactant selected from alkyl alcohols, ethers, esters and combinations of two or more of the foregoing, the method comprising:
    a) contacting a gaseous composition comprising the at least one reactant with carbon monoxide in a reaction zone under vapor-phase carbonylation reaction conditions in the presence of a catalyst comprising iridium and at least one second metal selected from gallium, zinc, indium and germanium, wherein the iridium and the at least one second metal are associated with a solid support material; and
    b) recovering at least one carboxylic acid or ester from the reaction zone, wherein the solid support material comprises activated carbon.

2. The method of claim 1 wherein the reaction zone is maintained at a pressure of from about 0.1 to about 100 bar absolute and a temperature of from about 100° C. to about 350° C.

3. The method of claim 1 wherein the catalyst further comprises at least one vaporous component comprising a halogen promoting component selected from hydrogen halides, gaseous hydrogen iodide, alkyl and aryl halides having up to 12 carbon atoms, iodine, bromine or chlorine, and mixtures of two or more of the foregoing.

4. The method of claim 3 wherein the at least one vaporous halogen promoting component is selected from hydrogen iodide, methyl iodide, ethyl iodide, 1-iodopropane, 2-iodobutane, 1-iodobutane, hydrogen bromide, methyl bromide, ethyl bromide, benzyl iodide and combinations of two or more of the foregoing.

5. The method of claim 3 wherein the at least one vaporous halogen promoting component is selected from hydrogen iodide, methyl iodide, hydrogen bromide, methyl bromide and combinations of two or more of the foregoing.

6. The method of claim 3 wherein the at least one reactant is methanol and the at least one vaporous halogen promoting component is present in an amount that results in a molar ratio of about 1:1 to 10,000:1 of methanol or methanol equivalents to halide.

7. The method of claim 1 wherein the at least one reactant is selected from an alkyl alcohol having from 1 to 10 carbon atoms, alkane polyols having 2 to 6 carbon atoms, alkyl alkylene polyethers having 3 to 20 carbon atoms, alkoxyalkanols having from 3 to 10 carbon atoms and combinations of two or more of the foregoing.

8. The method of claim 1 wherein the catalyst includes from about 0.1 weight percent to about 3 weight percent of the total catalyst weight each of the iridium and the at least one second metal.

9. The method of claim 1 wherein the molar ratio in the catalyst of the at least one second metal to iridium is from about 0.1:1 to about 10:1.

10. The method of claim 1 wherein the molar ratio in the catalyst of the at least one second metal to iridium is from about 0.5:1 to about 5:1.

11. A method for producing at least one carboxylic acid, ester, or combination of carboxylic acid and ester mixtures from at least one selected from alkyl alcohols, ethers, esters and combinations of two or more of the foregoing, the method comprising:
   a) contacting a gaseous composition comprising the at least one reactant with carbon monoxide in a reaction zone under vapor-phase carbonylation reaction conditions in the presence of a catalyst comprising from about 0.01 weight percent to about 10 weight percent of the total catalyst weight each of iridium and at least one second metal selected from gallium, zinc, indium and germanium, wherein the iridium and at least one second metal are associated with a solid support material; and
   b) recovering at least one carboxylic acid or ester from the reaction zone wherein the solid support material comprises activated carbon.

12. The method of claim 11 wherein the reaction zone is maintained at a pressure of from about 0.1 to about 100 bar absolute and a temperature of from about 100° C. to about 350° C.

13. The method of claim 11 wherein the catalyst further comprises at least one vaporous component comprising a halogen promoting component selected from hydrogen halides, gaseous hydrogen iodide, alkyl and aryl halides having up to 12 carbon atoms, iodine, bromine or chlorine, and mixtures of two or more of the foregoing.

14. The method of claim 13 wherein the at least one vaporous halogen promoting component is selected from hydrogen iodide, methyl iodide, ethyl iodide, 1-iodopropane, 2-iodobutane, 1-iodobutane, hydrogen bromide, methyl bromide, ethyl bromide, benzyl iodide and combinations of two or more of the foregoing.

15. The method of claim 13 wherein the at least one vaporous halogen promoting component is selected from hydrogen iodide, methyl iodide, hydrogen bromide, methyl bromide and combinations of two or more of the foregoing.

16. The method of claim 13 wherein the at least one reactant is methanol and the at least one vaporous halogen promoting component is present in an amount that results in a molar ratio of about 1:1 to 10,000:1 of methanol or methanol equivalents to halide.

17. The method of claim 11 wherein the at least one reactant is selected from an alkyl alcohol having from 1 to 10 carbon atoms, alkane polyols having 2 to 6 carbon atoms, alkyl alkylene polyethers having 3 to 20 carbon atoms, alkoxyalkanols having from 3 to 10 carbon atoms and combinations of two or more of the foregoing.

18. The method of claim 11 wherein the catalyst includes from about 0.1 weight percent to about 3 weight percent of the total catalyst weight each of the iridium and the at least one second metal.

19. The method of claim 11 wherein the molar ratio in the catalyst of the at least one second metal to iridium is from about 0.5:1 to about 5:1.

* * * * *